(12) United States Patent
Verzini et al.

(10) Patent No.: US 9,481,635 B2
(45) Date of Patent: Nov. 1, 2016

(54) PROCESS FOR PREPARING GABAPENTIN

(71) Applicant: ZACH SYSTEM S.P.A., Bresso (MI) (IT)

(72) Inventors: Massimo Verzini, Caldiero (IT); Livius Cotarca, Cervignano del Friuli (IT); Fabio Belluzzo, San Bonifacio (IT); Giorgio Soriato, Caldiero (IT); Daniele Urbani, Lendinara (IT); Enrico Pace, Bresso (IT)

(73) Assignee: ZACH SYSTEM S.P.A., Bresso (MI) (IT)

( * ) Notice: Subject to any disclaimer, the term of this patent is extended or adjusted under 35 U.S.C. 154(b) by 0 days.

(21) Appl. No.: 15/028,723

(22) PCT Filed: Oct. 21, 2014

(86) PCT No.: PCT/EP2014/072564
§ 371 (c)(1),
(2) Date: Apr. 12, 2016

(87) PCT Pub. No.: WO2015/059150
PCT Pub. Date: Apr. 30, 2015

(65) Prior Publication Data
US 2016/0237025 A1    Aug. 18, 2016

(30) Foreign Application Priority Data
Oct. 22, 2013 (IT) .............................. MI2013A1757

(51) Int. Cl.
*C07C 227/18* (2006.01)
*C07C 227/40* (2006.01)
*C07C 227/42* (2006.01)

(52) U.S. Cl.
CPC ........... *C07C 227/18* (2013.01); *C07C 227/40* (2013.01); *C07C 227/42* (2013.01)

(58) Field of Classification Search
CPC .. C07C 227/18; C07C 227/40; C07C 227/42
See application file for complete search history.

(56) References Cited

U.S. PATENT DOCUMENTS

| 4,024,175 A | 5/1977 | Satzinger et al. |
| 5,068,413 A | 11/1991 | Steiner et al. |
| 5,091,567 A | 2/1992 | Geibel et al. |
| 6,518,456 B1 | 2/2003 | Peverali et al. |
| 7,393,974 B2 | 7/2008 | Ferrari et al. |
| 2007/0066843 A1* | 3/2007 | Arrighi ............... C07C 231/02 562/504 |
| 2007/0293700 A1* | 12/2007 | Giovanetti ............ C07C 227/04 562/507 |
| 2008/0103334 A1* | 5/2008 | Kumar .................. C07C 227/04 562/507 |

FOREIGN PATENT DOCUMENTS

| EP | 2368872 A1 | 9/2011 |
| WO | 9828255 A1 | 7/1998 |
| WO | 0234709 A1 | 5/2002 |
| WO | 2008106217 A1 | 9/2008 |

OTHER PUBLICATIONS

International Search Report of PCT/EP2014/072564 of Jan. 27, 2015.
Written Opinion of PCT/EP2014/072564 of Jan. 27, 2015.

* cited by examiner

*Primary Examiner* — Shailendra Kumar
(74) *Attorney, Agent, or Firm* — Silvia Salvadori, P.C.; Silvia Salvadori

(57) ABSTRACT

The present invention relates to a process for preparing gabapentin and, more particularly, it relates to a process for the direct extraction of gabapentin from an aqueous solution derived from the Hofmann rearrangement of 1,1-cyclohexanediacetic acid monoamide.

10 Claims, No Drawings

PROCESS FOR PREPARING GABAPENTIN

This application is a U.S. national stage of PCT/EP2014/072564 filed on 21 Oct. 2014, which claims priority to and the benefit of Italian Application No. MI2013A001757 filed on 22 Oct. 2013, the contents of which are incorporated herein by reference in their entireties.

The present invention relates to a process for preparing gabapentin and, more particularly, it relates to a process for the direct extraction of gabapentin from an aqueous solution derived from the Hofmann rearrangement of 1,1-cyclohexanediacetic acid monoamide.

Gabapentin, namely, 1-(aminomethyl)-cyclohexaneacetic acid (The Merck Index, XII ed., page 733, No. 4343), is a known drug with anti-epileptic activity which was described for the first time in U.S. Pat. No. 4,024,175 by Warner-Lambert Co.

Several processes for the preparation of gabapentin have been reported in the literature, see, for instance, the already cited U.S. Pat. No. 4,024,175, U.S. Pat. No. 5,068,413 and U.S. Pat. No. 5,091,567, both in the name of Godecke AG.

Substantially all these methods involve the isolation of a gabapentin salt and a final purification phase which consists in treating an aqueous solution of said salt (generally the hydrochloride) through a weak basic ion exchange resin, total evaporation of the water from the aqueous gabapentin solution eluted from the resin and crystallization from an alcoholic solvent, generally, methanol or a methanol/isopropanol or an ethanol/ether mixtures.

U.S. Pat. No. 4,024,175 describes various processes for preparing gabapentin or similar compounds of formula

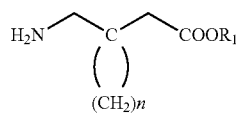

wherein $R_1$ is a hydrogen atom or a lower alkyl and n is 4, 5 or 6; characterized by the use of conventional methods for preparing primary amines or amino acids, for instance, the Curtius, Hofmann and Lossen rearrangements.

In particular, in the above mentioned patent in the name of Warner Lambert Co., Example 4 variant A, column 5 describes the synthesis of the lower cyclic homologue derivative of gabapentin, namely, 1-(methylamino)-1-cyclopentaneacetic acid, via the Hofmann rearrangement of 1,1-cyclopentanediacetic acid monoamide performed in the presence of sodium hypobromite, acidification and extraction followed by a final phase of purification of the hydrochloride salt obtained which consists in eluting through a basic ion-exchange resin and recrystallization from alcohols.

International patent application WO 02/034709 in the name of the same Applicant describes the synthesis of gabapentin via the Hofmann rearrangement of 1,1-cyclohexanediacetic acid monoamide in the presence of sodium hypochlorite, acidification, extraction, purification of the gabapentin hydrochloride obtained through a strong cationic resin and recrystallization.

In particular, Example 1 describes the specific extraction with n-butanol and the simultaneous acidification of the reaction mixture obtained from said Hofmann rearrangement; water is added to the combined organic phases and the two-phase solution is purified through a column containing a strong cationic resin.

Several alternative methods to the use of the ion-exchange resin for the conversion of gabapentin hydrochloride into gabapentin have been also described.

International patent application WO 98/28255 (Teva) describes a process for preparing gabapentin from the corresponding hydrochloride which comprises the purification of gabapentin hydrochloride from mineral salts derived from the synthesis by (a) dissolving gabapentin hydrochloride in organic solvents in which the mineral salts are insoluble, (b) filtering and (c) optionally evaporating off the solvent; treating a solution of gabapentin hydrochloride with an amine in a solvent so that gabapentin form III precipitates out and crystallizing to obtain gabapentin form II.

U.S. Pat. No. 7,393,974 (Erregierre S.p.A.) describes a process for converting gabapentin hydrochloride into free gabapentin which comprises the dissolution of said salt in a suitable solvent and treatment with an amine, in particular dicyclohexylamine, so as to precipitate out the corresponding addition salt and leave the free gabapentin in solution.

WO 2008/106217 (Teva) describes a process for converting gabapentin hydrochloride into free gabapentin which comprises the extraction of said salt with $C_4$-$C_7$ alcohols and treatment with an amine, in particular tributylamine, so as to precipitate out free gabapentin from the mixture.

U.S. Pat. No. 6,518,456 (Procos S.p.A.) describes the neutralization of gabapentin hydrochloride with a base such as sodium hydroxide at the isoelectric point of gabapentin, i.e. pH 7.2, allowing the precipitation and isolation from water of crude gabapentin monohydrate via filtration.

Although several methods for preparing and purifying gabapentin are known in the art, they suffer from some drawbacks.

Processes based on the use of 1,1-cyclohexanediacetic acid derivatives lead predominantly, if not exclusively, to the preparation of a gabapentin salt dissolved in aqueous solution.

For cost reasons, the intermediate gabapentin hydrochloride is generally produced in industrial practice; the isolation of gabapentin from the corresponding hydrochloride is performed at the industrial level via several processes, but all the techniques used have the drawback of passing through countless operating units, of generating a large amount of saline scraps and lead to a consistent loss of yield.

Such solutions containing the intermediate salt constitute large volumes of liquid that are unsuitable from the point of view of the industrial application of the process.

In addition, one of the main problems relating to the disposal of the scraps produced by such processes is linked to the enormous amount of mineral anions contained therein.

Said intermediate salt must necessarily be converted into pure gabapentin by means of purification methods among which the one most commonly used at the industrial level is undoubtedly the passage through ion-exchange resins.

In other cases, as described above, the neutralization of the corresponding gabapentin addition acid takes place via the use of a base.

Besides producing pure gabapentin, the various treatments are directed towards reducing the content of the mineral salts produced in the isolation phase.

The mineral salts present in the gabapentin aqueous solution are generally sodium salts, for instance, sodium chloride.

Recently, it has been sought to avoid the preparation of said gabapentin intermediate salts in order to appreciably simplify the industrial procedure.

Patent application EP 2368872 (Serichim) describes a process for preparing gabapentin via the Hofmann rearrangement of cyclohexanediacetic acid monoamide and extraction of said gabapentin from the reaction mixture with a $C_4$-$C_7$ aliphatic alcohol.

The experimental section is exclusively devoted to the extraction method via the continuous or batch use of n-butanol.

Said application, thus, proposes to avoid the conventional purification cycle (in particular column chromatography) by extracting free gabapentin directly from the Hofmann end mixture.

However, the capacity for extracting gabapentin from said mixture with n-butanol proves to be unsuitable for an industrial application since it obliges the use of appreciable amounts of solvents and/or of extraction cycles.

In addition, the solution of gabapentin in n-butanol obtained from the extraction process shows a high content of mineral salts which crystallize with gabapentin following the removal of water from the butanol solution via azeotropic distillation. Crystallized gabapentin must, therefore, necessarily be subjected to purification cycles to obtain a product that is in line with pharmacopoiea specifications.

Therefore, the technical problem underlying the present invention is that of identifying an improved solvent system that would extract gabapentin efficiently and selectively from the Hofmann end aqueous solution and that would, at the same time, avoid transferring into the organic phase the undesired mineral salts (in primis sodium chloride).

It is consequently necessary to study novel methods that allow the process of synthesis of free gabapentin to be performed in reduced times, limiting the apparatus present in the system and under conditions that make it possible to produce a final product in high yields and in a purity that is suitable for pharmaceutical use.

We have now, surprisingly, found a process for preparing gabapentin at the industrial level which makes it possible, via the direct extraction of gabapentin from a suitable solvent, to overcome the drawbacks of the processes described in the art.

Thus, an object of the present invention is a process for preparing gabapentin which comprises:

a) Hofmann rearrangement of 1,1-cyclohexanediacetic acid monoamide;

b) neutralizing the reaction mixture obtained by said rearrangement;

c) extracting gabapentin from said reaction mixture with phenol optionally mono- or di-substituted by a ($C_1$-$C_4$)-alkyl group; and d) isolating the product.

The process object of the present invention involves a first phase (step a) in which the Hofmann rearrangement of 1,1-cyclohexanediacetic acid monoamide is performed according to known techniques.

Preferably, the Hofmann rearrangement of the monoamide is performed according to the method described in the International Patent Application WO 02/034709, already cited, in the name of the same Applicant.

In one aspect of the invention, said monoamide dissolved in a mixture of water and sodium hydroxide is added portionwise to an aqueous solution of sodium hydroxide and sodium hypohalite, preferably sodium hypochlorite, prepared beforehand while keeping the temperature under strict control. At the end of the reaction, removal of the excess oxidizing power is performed by using a reducing agent, for instance, sodium metabisulfite.

The reaction mixture obtained at the end of the Hofmann rearrangement has a strongly basic pH and is, mainly, composed of gabapentin sodium salt in carbamate form, sodium halide and traces of sodium hydroxide.

The process object of the present invention involves neutralization of the Hofmann end mixture (step b) by adjusting the pH to an optimum value for the precipitation of the amino acid, gabapentin, in the form of the internal salt (isoelectric point).

Preferably, the reaction mixture is neutralized at a pH of between 6.9 and 7.5 and, even more preferably, at about a value of 7.2, i.e. at the pH value corresponding to the isoelectric point of gabapentin.

Operatively, it is preferred to perform a more resolute acidification by bringing the pH of the Hofmann end mixture to a value of about 4-5 so as to promote the decarboxylation of the carbamate of gabapentin and, subsequently, to adjust the pH to around the isoelectric point by using a base, among which the preferred is sodium hydroxide.

The neutralization reaction of the aqueous mixture obtained from said Hofmann rearrangement may be performed using known organic or mineral acids, for instance, acetic acid, citric acid, hydrochloric acid, formic acid, maleic acid, methanesulfonic acid, oxalic acid and tartaric acid or, optionally, mixtures thereof.

The acids are generally used in the reaction in pure form, in aqueous solution or in the gas phase.

Purely for the purposes of process economy, the neutralization phase is, preferably, performed with mineral acids and, usually, with hydrochloric acid in pure form or, preferably, in aqueous solution.

The neutralization reaction is performed at room temperature for easier and more economic management of the process.

Optionally, said neutralization phase comprises a pre-extraction of the aqueous mixture with suitable solvents such as hydrocarbons, esters and ethers the preferred being toluene, ethyl acetate, isopropyl acetate and MTBE (methyl tert-butyl ether).

Said pre-extraction with a suitable solvent makes it possible to remove many of the impurities contained in the complex aqueous solution obtained from the Hofmann rearrangement; impurities which would otherwise be entrained into the end product.

In a preferred aspect of the invention, the process is performed with a more resolute acidification of the mixture at room temperature so as to bring the pH of the Hofmann end mixture to a value of between 4-5; once said pH value is reached, the solution is heated to about 40° C., cooled to room temperature and a suitable solvent is added; the mixture is stirred for about 30 minutes followed by separating out the aqueous phase, which is brought to a pH of about 7.2 with a base, preferably, sodium hydroxide.

Gabapentin extraction phase (step c) involves adding phenol optionally mono- or di-substituted with a ($C_1$-$C_4$)-alkyl group to the aqueous solution obtained from the Hofmann rearrangement, appropriately, neutralized as described above.

In the present invention, the term ($C_1$-$C_4$)-alkyl group means a methyl, ethyl, n-propyl, isopropyl, n-butyl, isobutyl, sec-butyl or tert-butyl group.

In the present invention, the term phenol optionally mono- or di-substituted with a ($C_1$-$C_4$)-alkyl group means phenol; mono-substituted derivatives thereof, for instance, 3-methylphenol (meta-cresol), 4-methylphenol (para-cresol), 2-methylphenol (ortho-cresol), 3-ethylphenol and 2-tert-butylphenol; di-substituted derivatives thereof, for instance, 2,3-dimethylphenol, 2,5-dimethylphenol, 3,5-dimethylphenol, 2,6-dimethylphenol, 2,4-dimethylphenol and 3,4-dimethylphenol; and mixtures thereof.

Preferably, gabapentin extraction phase (step c) is performed with a phenol mono-substituted with a ($C_1$-$C_4$)-alkyl group.

Even more preferably, gabapentin extraction phase (step c) is performed with a mono-substituted phenol selected from 3-methylphenol (meta-cresol), 4-methylphenol (para-cresol), 2-methylphenol (ortho-cresol), 3-ethylphenol, 2-tert-butylphenol and mixtures thereof; 3-methylphenol (meta-cresol) being even more preferred.

It is clear to a person skilled in the art that said appropriately neutralized aqueous solution obtained from the Hofmann rearrangement may be in suspension form following the precipitation of part of the gabapentin internal salt.

In this manner, gabapentin is directly transferred into the organic phase by leaving the mineral salts in the aqueous solution which is immediately discarded.

Said organic phase, i.e. a solution of gabapentin in phenol or derivatives thereof, may be appropriately anhydrified in order to remove the undesired saline impurities contained in the aqueous residue via a simple filtration.

To this end, in a preferred aspect of the invention, said solution of gabapentin in phenol or derivatives thereof obtained in the extraction phase is anhydrified via distillation leading to the precipitation of the mineral salts still present (opalescence); filtration and optional washing with demineralized water lead to a solution of gabapentin in phenol or derivatives thereof in which the mineral salts and, mainly, the chlorides are detectable in a few tens of parts per million (ppm).

Operatively, the process is performed by distillation of the solution of gabapentin in phenol or derivatives thereof under vacuum while keeping the temperature at about 40° C. for a few hours; the solution is then cooled to room temperature, suitably filtered and, optionally, washed with demineralized water.

Alternatively, the saline impurities may be removed via multiple extractions of the organic solution of gabapentin with water until an optimal saline concentration in the organic phase of ppm order is reached.

In a preferred aspect of the invention, the appropriately neutralized Hofmann solution is extracted with phenol or derivatives thereof added in a volume ratio of at least 0.3 relative to the aqueous solution of gabapentin.

Preferably, phenol or derivatives thereof are added in a volume ratio of between 0.6-0.9 relative to the aqueous solution of gabapentin.

In line with the physical characteristics of the solvent or mixture of solvents used, the extraction reaction is generally performed at a temperature of between 0 and 80° C.; preferably, the extraction temperature is between 20 and 50° C. for easier and more economic management of the process.

The isolation of the product according to the invention (step d) substantially comprises a separation of gabapentin from the solution of phenol or derivatives thereof.

Said separation may generally be performed by contro-extraction or, alternatively, direct crystallization of gabapentin.

Thus, in one aspect of the invention, the organic phase obtained from the extraction step c, consisting predominantly of a solution of gabapentin in phenol or derivatives thereof, is contro-extracted with water to give a two-phase system; the aqueous phase containing gabapentin is then separated out and the spent organic solvent is conveyed for recovery. It is clear to a person skilled in the art that to increase the efficacy of the process according to the invention, it may be appropriate to use techniques suited to increasing the affinity of the solute, gabapentin, for the aqueous phase, for instance, the addition of a suitable antisolvent or, alternatively, to perform a contro-extraction of the gabapentin solution via the use of an ammonia aqueous solution.

In one aspect of the invention, said contro-extraction of the gabapentin solution is performed by using an ammonia aqueous solution, preferably, with a concentration of about 10% w/w.

In a preferred aspect of the invention, said contro-extraction of the gabapentin solution is performed by adding water, preferably demineralized water, and a suitable antisolvent.

Antisolvent according to the invention is a solvent belonging to the family of hydrocarbons, among which toluene and cyclohexane are preferred; esters, among which ethyl acetate and isopropyl acetate are preferred; ethers, MTBE being preferred; and chlorinated solvents such as dichloromethane.

More preferred antisolvents are MTBE, isopropyl acetate and ethyl acetate.

In a preferred aspect of the invention, the solution of gabapentin in phenol or derivatives thereof is extracted with water and an antisolvent in a volumetric ratio of between 1-3/1 water/phenolic solution and/or 1-3/1 organic solvent/phenolic solution.

Preferably, the solution of gabapentin in phenol or derivatives thereof is extracted with water and an antisolvent in a volumetric ratio of 1/2/2.3 phenolic solution/water/organic solvent.

In one aspect of the invention, the aqueous phase containing gabapentin obtained after the contro-extraction is, optionally, treated with a solvent suitable for extracting out any small portions of cresol residue remaining therein.

Solvents suitable for said washing are substantially those optionally used as antisolvents in the phase of contro-extraction in water described above and preferably MTBE, ethyl acetate and isopropyl acetate.

Said aqueous phase containing gabapentin obtained after the contro-extraction is concentrated and gabapentin may be isolated via, for example, cold filtration.

In an alternative aspect of the invention, the organic phase obtained from the extraction step c, consisting predominantly of a solution of gabapentin in phenol or derivatives thereof, is supplemented with a suitable antisolvent so as to lead to the direct crystallization of gabapentin which is isolated by filtration.

Antisolvents suitable for said crystallization are substantially those optionally used as antisolvents in the phase of contro-extraction in water described above and preferably MTBE, ethyl acetate and isopropyl acetate.

In one aspect of the invention, it is preferred to take up the residue derived from the phase of concentration of the aqueous solution of gabapentin or, alternatively, through the direct crystallization with a suitable solvent or mixture of solvents, preferably aliphatic alcohols, according to conventional techniques.

Operatively, methanol is added to the aqueous solution of gabapentin obtained in the isolation phase appropriately concentrated by distillation or to the crystalline residue, while raising the temperature to about 50-55° C.; this temperature is maintained for about 1 hour and the solution is then cooled to about 25° C. followed by the introduction of isopropanol; the solution is then cooled and the residue obtained is filtered and washed to give gabapentin in high yields.

Alternatively, isopropanol is added to the aqueous solution of gabapentin obtained in the isolation phase appropriately concentrated by distillation or to the crystalline residue, while raising the temperature to about 40° C.; this temperature is maintained for about 1 hour and the solution is then cooled and the residue obtained is filtered and washed to give gabapentin in high yields.

Gabapentin thus isolated is optionally subjected to re-crystallization from organic solvents according to conventional techniques.

Preferably, the re-crystallization phase is performed from alcohols and even more preferably from mixtures such as methanol/isopropanol.

It is evident that the extraction process object of the present invention may be readily performed in batch mode or continuously according to conventional techniques.

The process object of the present invention makes it possible to obtain gabapentin directly from the aqueous solution derived from the Hofmann rearrangement.

There is no doubt that the preparation methods involving the isolation of gabapentin in salified form are efficient from the industrial point of view, but they necessitate an additional synthetic step in order to convert gabapentin salt into the free amino acid.

Thus, one of the practical advantages derived from the process described herein above is that it completely eliminates the conventional purification cycle, by directly isolating gabapentin in a high degree of purity suitable for pharmaceutical specifications.

In addition, the attempts described in the art to extract gabapentin from the Hofmann end mixture have, to date, proven to be inefficient from an industrial viewpoint.

A direct comparison with the closest prior art, i.e. the above mentioned patent application EP 2368872, makes it possible to reveal the technical advantages afforded by the extraction of gabapentin from phenol or derivatives thereof according to the present invention.

Firstly, the solvent object of the present invention, when compared with n-butanol described in the art, has an appreciably better capacity for extracting gabapentin thanks to a distribution ratio between the organic phase and the saline aqueous phase obtained at the end of the Hofmann rearrangement that is several tens of times higher. This characteristic makes it possible to totally extract gabapentin from a Hofmann end solution with an amount of solvent that is considerably lower compared with n-butanol and/or with a reduced number of extractions.

In addition, the solution of gabapentin in phenol or derivatives thereof after extraction of the appropriately neutralized Hofmann end mixture has a chloride content that is substantially smaller than that of the corresponding solution of gabapentin in n-butanol. Thus, the use of the solvent according to the invention compared to n-butanol has the advantage of reducing the saline component extracted from the Hofmann end solution by the organic solvent.

Said saline component is further reduced by means of the physico-chemical characteristics of the solvent object of the present invention.

For example, gabapentin in anhydrous cresol has a solubility of about 20% whereas the solubility in n-butanol is virtually zero. Thus, the solution of gabapentin in cresol after extraction may be anhydrified, for example, by distillation so as to crystallize the undesired residual salts leaving the gabapentin itself in solution. Said solution of gabapentin in cresol obtained from the removal of the salts by filtration and/or by contro-extraction with water has a chloride content of a few tens of ppm.

The same technique cannot be applied to the corresponding solution in n-butanol of the prior art, since the solubility of gabapentin in the anhydrous solvent is very low; as a result the butanolic solution of gabapentin extraction from the Hofmann end solution, when subjected to anhydrification reaction, leads to the co-precipitation of gabapentin and of these same salts, thus, with no advantage from the point of view of product purity.

Attention is drawn to the industrial implementation of the process described in the experimental section of International patent application WO 02/034709, already mentioned, in the name of the same Applicant, where following an extraction phase with n-butanol (Example 1), salification to the hydrochloride salt and subsequent purification of the product via column chromatography are mandatory.

Attention is further drawn to the high purity of gabapentin obtained via the process object of the present invention when compared with gabapentin crystallized from n-butanol according to the procedure described in EP '872 (titre: 100% with a chloride content of less than 50 ppm; as opposed to titre: 90% with a chloride content of about 34.000 ppm).

Said gabapentin purity makes it possible to consider as purely optional any re-crystallization procedure from alcohols known in the art.

Therefore, the process object of the present invention makes it possible to obtain gabapentin efficiently, in a high purity, without appreciable variations in yield, in a lower number of synthetic steps than the conventional methods and, consequently, with reduced times and costs.

In addition, the use of reagents and solvents is appreciably limited with further advantages regarding the disposal of the industrial scraps.

It is therefore evident how the process object of the present invention is advantageous when compared with those already described in the literature.

A practical embodiment of the process object of the present invention comprises the Hofmann rearrangement of 1,1-cyclohexanediacetic acid monoamide; neutralization of the reaction mixture obtained from said rearrangement; extraction of said neutralized mixture with phenol or derivatives thereof; isolation of gabapentin; and optional re-crystallization from alcohols.

A preferred practical embodiment of the process object of the present invention comprises the Hofmann rearrangement of 1,1-cyclohexanediacetic acid monoamide; neutralization of the reaction mixture obtained from said rearrangement by acidification, washing with a suitable solvent and adjusting the pH to an appropriate value with a base; extraction of said neutralized mixture with phenol or derivatives thereof, followed by distillation of the organic solution, filtration and washing with water; isolation of gabapentin via contro-extraction with water and antisolvent; washing of the aqueous solution followed by concentration, addition of alcohols, filtration, drying and optional recrystallization from alcohols.

For the purpose of better illustrating the present invention the following examples are now given.

EXAMPLE 1

Hofmann Reaction and Decarboxylation 100 g of Gaba 1 (1,1-cyclohexanediacetic acid monoamide) were placed in a 1 liter reactor at room temperature, followed by addition of 76 g of demineralized water. While maintaining the temperature at about 20° C., 74 g of a caustic sodium hydroxide solution were added. The mixture was stirred vigorously until dissolution was complete. In parallel, 70 g of a caustic sodium hydroxide solution and, then, 288 g of a 14% sodium hypochlorite solution were placed in a 2 liter reactor. The sodium hypochlorite solution was cooled to −10° C. and, when this temperature had been reached, the solution of Gaba 1 was added over about 2 hours, while maintaining the temperature at about −10° C. The temperature was raised to about 20° C. over about 2 hours. This temperature was maintained for 2 hours and sodium metabisulfite was, then, added until the oxidizing power had completely disappeared. The basic pH of the reaction mixture was brought to 4.5-5 with a hydrochloric acid solution, while maintaining the temperature at about 20° C. When this pH was reached, the solution was heated to about 40° C. This temperature was maintained for 20-30 minutes and the solution was, then, cooled to about 20° C. 150 g of ethyl acetate were added and the mixture was, then, stirred for 1 hour and then left to stand until the phases had separated. The upper organic phase was discarded and 150 g of ethyl acetate were added to the aqueous phase. The mixture was stirred for 1 hour and, then, left to stand until the phases had separated. The upper organic phase was discarded and the aqueous phase was brought to pH 7.2 with a caustic sodium hydroxide solution.

Extraction with m-Cresol and Gabapentin Isolation:

430 g of m-cresol were added to the gabapentin solution/suspension (crystallized gabapentin). The mixture was stirred for 1 hour and, then, left to stand until the phases had separated. The lower aqueous phase was discarded and the organic phase was distilled under vacuum to a constant water content in the cresol mixture. The solution was cooled to about 20° C. and the opalescent solution was, then, filtered through a filter system. 150 g of demineralized water were added to the filtered solution. The mixture was stirred for about 15 minutes and, then, left to stand until the phases had separated. The aqueous phase was discarded and 894 g of ethyl acetate and 1167 g of demineralized water were added to the organic solution. The mixture was stirred for about 15 minutes and, then, left to stand until the phases had separated. The organic phase was discarded and 150 g of ethyl acetate were added to the aqueous phase. The mixture was stirred for about 15 minutes and, then, left to stand until the phases had separated. The organic phase was discarded and 3-4 g of Carbon L4S were added to the aqueous phase. The mixture was stirred, heated to 35-40° C. and, then, filtered. The filtered solution was concentrated under vacuum to a solid residue and the mixture was, then, cooled to about 20° C. and 61 g of methanol were added. This mixture was heated to 50-55° C. and maintained until homogenization of the solid was complete. The resulting mixture was cooled to about 25° C. and, once this temperature had been reached, 254 g of isopropanol were added. The resulting mixture was maintained at about 25° C. for about 20 minutes. It was cooled to −3--−5° C. and, once at this temperature, was maintained for at least 1 hour and the mixture was, then, filtered. The product was washed on a filter twice with isopropanol. The wet product was dried under vacuum to constant weight. 62 g of "pure" gabapentin were obtained (titre: 100%).

[HPLC analysis: m-cresol: 0.000%; max. single impurity: 0.003%; total impurities: 0.003%; chlorides: not detectable]

EXAMPLE 2

Hofmann Reaction and Decarboxylation 200 g of Gaba 1 (1,1-cyclohexanediacetic acid monoamide) and 152 g of demineralized water were placed in a 1 liter reactor at room temperature. While maintaining the temperature at about 20° C., 148 g of a caustic sodium hydroxide solution were added. The mixture was stirred vigorously until dissolution was complete. In parallel, 139 g of a caustic sodium hydroxide solution and, then, 571 g of a 14% sodium hypochlorite were placed in a 2 liter reactor. The sodium hypochlorite solution was cooled to −10° C. and, while maintaining the temperature, the solution of Gaba 1 was then added over about 2 hours. The temperature was raised to about 20° C. over about 2 hours. The temperature was maintained for 2 hours and sodium metabisulfite was, then, added until the oxidizing power had completely disappeared. The basic pH was brought to 4.5-5 with a hydrochloric acid solution, while maintaining the temperature at about 20° C. When this pH had been reached, the solution was heated to about 40° C. The mixture was maintained at this temperature for 20-30 minutes and, then, cooled to about 20° C. 200 g of isopropyl acetate were added to the aqueous solution of gabapentin and the mixture was stirred for 1 hour and, then, left to stand until the phases had separated. The upper organic phase was discarded and the aqueous phase was brought from pH 4.5-5 to around pH 7.2 with caustic sodium hydroxide.

Extraction with m-Cresol and Gabapentin Isolation:

860 g of m-cresol were added to the gabapentin solution/suspension (crystallized gabapentin). The mixture was stirred for 1 hour and, then, left to stand, and the lower aqueous phase was, then, discarded. The organic phase was distilled under vacuum to a constant water content in the cresol mixture. The solution was cooled to about 20° C. and the opalescent solution was, then, filtered through a filter system. 200 g of demineralized water were added to the organic phase and the mixture was stirred for about 15 minutes. It was left to stand until the phases had separated, the lower aqueous phase was, then, discarded and 1788 g of isopropyl acetate and 2334 ml of demineralized water were added to the organic solution. The mixture was stirred for about 30 minutes and, then, left to stand until the phases had separated. The organic phase was discarded and 300 g of isopropyl acetate were added to the aqueous phase. The mixture was stirred for 30 minutes and, then, left to stand until the phases had separated. The organic phase was discarded and the aqueous phase was concentrated under vacuum to a solid residue. The mixture was cooled to about 20° C. and 112 g of methanol were added. This mixture was heated to 50-55° C. and maintained until homogenization of the solid was complete. The resulting mixture was cooled to about 25° C. and, at this temperature, 464 g of isopropanol were added. The mixture was maintained at about 25° C. for about 20 minutes and, then, cooled to −3 to −5° C. At this temperature, the solid was isolated by filtration. The gabapentin was washed twice with isopropanol. The wet product was dried under vacuum to constant weight. 135 g of "pure" gabapentin were obtained (titre: 100%).

[HPLC analysis: m-cresol: 0.000%; max. single impurity: 0.014%; total impurities: 0.030%; chlorides: not detectable]

EXAMPLE 3

Hofmann Reaction and Decarboxylation 100 g of Gaba 1 (1,1-cyclohexanediacetic acid monoamide) and 76 g of demineralized water were placed in a 1 liter reactor at room temperature. While maintaining the temperature at about 20° C., 73 g of a caustic sodium hydroxide solution were added. In parallel, 69 g of a caustic sodium hydroxide solution and, then, 279 g of a 14% solution of sodium hypochlorite were placed in a 2 liter reactor. The sodium hypochlorite solution was cooled to −10° C. and, while maintaining the solution at this temperature, the solution of Gaba 1 was added over about 2 hours. The temperature was raised to about 20° C. over about 2 hours and maintained for 2 hours. Sodium metabisulfite was added until the oxidizing power had completely disappeared. The basic pH of the solution was brought to 4.5-5 with a hydrochloric acid solution, while maintaining the temperature at about 20° C. Once the desired pH had been reached, the solution was brought to about 40° C. and maintained at this temperature for 20-30 minutes. The mixture was cooled to about 20° C. and 100 g of MTBE were added. The mixture was stirred for about 30 minutes and left to stand until the phases had separated. The organic phase was discarded and the aqueous phase was brought from pH 4.5-5 to about pH 7.2 with a caustic sodium hydroxide solution.

Extraction with m-Cresol and Crude Gabapentin Isolation:

430 g of m-cresol were added to the gabapentin solution/suspension (crystallized gabapentin). The mixture was stirred for 1 hour and, then, left to stand until the phases had separated. The lower aqueous phase was discarded and the organic phase was distilled under vacuum to a constant water content in the cresol mixture. The solution was cooled to about 20° C. and the opalescent solution was, then, filtered through a filter system. 894 g of MTBE and 1167 ml of demineralized water were added to the filtered solution. The mixture was stirred for about 30 minutes and, then, left to stand until the phases had separated. The organic phase was discarded and 150 g of MTBE were added to the aqueous phase. The mixture was stirred for about 30 minutes and left to stand until the phases had separated. The organic phase was discarded and the aqueous phase was concentrated under vacuum to a solid residue. The mixture was cooled to about 20° C. and 211 g of isopropanol were, then, added. The mixture was heated to about 40° C. and maintained at this temperature for about 1 hour. The resulting mixture was cooled to about −5° C. and the solid was, then, isolated by filtration. The product was washed on a filter twice with isopropanol. The product was dried under vacuum to constant weight. 72 g of crude gabapentin were obtained.

[HPLC analysis: m-cresol: 0.000%; max. single impurity: 0.113%; total impurities: 0.173%; chlorides: 15 ppm]

Purification:

72 g of crude gabapentin (obtained according to the procedure described above), 27 g of demineralized water and 50 g of methanol were placed in a 1 liter reactor. The suspension was heated to 50-55° C. and maintained at this temperature for 15-30 minutes. The suspension was cooled to about 25° C. 206 g of isopropanol were added at this temperature. The mixture was maintained at about 25° C. for about 20 minutes and, then, cooled to about −3-−5° C. At this temperature, the solid was isolated by filtration. The solid was washed twice with isopropanol. The wet product was dried under vacuum to constant weight. 68 g of "pure" gabapentin were obtained (titre: 100%).

[HPLC analysis: m-cresol: 0.000%; max. single impurity: 0.002%; total impurities: 0.003%; chlorides: not detectable]

EXAMPLE 4

According to the procedure described in Example 1 above, after the extraction with m-cresol and drying by distillation, an organic solution of gabapentin was obtained, to which were added 894.2 g of ethyl acetate over about 2 hours and at a temperature around 40° C. Once the addition was complete, the reaction mixture was cooled to about 20° C., filtered and the product was washed with 10 g of ethyl acetate to give 130 g of wet gabapentin.

Purification:

130 g of crude wet gabapentin (obtained according to the procedure described above), 32.3 g of demineralized water and 59 g of methanol were placed in a 1 liter reactor. The suspension was heated to 50-55° C. and maintained at this temperature for 15-30 minutes. The suspension was cooled to about 25° C. 244 g of isopropanol were added at this temperature. The mixture was maintained at about 25° C. for about 20 minutes and, then, cooled to −3-−5° C. At this temperature, the solid was isolated by filtration. The solid was washed twice with isopropanol. The wet product was dried under vacuum to constant weight. 67 g of "pure" gabapentin were obtained (titre: 100%).

The invention claimed is:

1. A process for preparing gabapentin which comprises:
    a) Hofmann rearrangement of 1,1-cyclohexanediacetic acid monoamide;
    b) neutralising the reaction mixture obtained by said rearrangement;
    c) extracting gabapentin from said reaction mixture with phenol optionally mono- or di-substituted by a ($C_1$-$C_4$)-alkyl group; and
    d) isolating the product.

2. A process according to claim 1 wherein said neutralising is carried out by adjusting pH to a value of 7.2.

3. A process according to claim 1 wherein said extracting is carried out with a phenol mono-substituted by a ($C_1$-$C_4$)-alkyl group.

4. A process according to claim 3 wherein said extracting is carried out with meta-cresol.

5. A process according to claim 1 wherein in said extracting the ratio between said phenol optionally mono- or di-substituted by a ($C_1$-$C_4$)-alkyl group and the neutralized mixture is comprised between 0.6 and 0.9 v/v.

6. A process according to claim 1 wherein said extracting further comprises an anhydrification reaction of the gabapentin organic solution.

7. A process according to claim 1 wherein said isolating is carried by contro-extracting gabapentin by adding water and an antisolvent.

8. A process according to claim 7 wherein said antisolvent is selected between ethyl acetate, MTBE and isopropyl acetate.

9. A process according to claim 7 wherein in said isolating the ratio between gabapentin organic solution/water/antisolvent is 1/2/2.3 v/v.

10. A process according to claim 7, wherein said isolating further comprises the concentration of the gabapentin aqueous solution obtained by said contro-extracting, the addition of an alcoholic solvent to the obtained residue and the product filtration.

* * * * *